United States Patent [19]

Kambin

[11] Patent Number: 5,480,440
[45] Date of Patent: * Jan. 2, 1996

[54] OPEN SURGICAL TECHNIQUE FOR VERTEBRAL FIXATION WITH SUBCUTANEOUS FIXATORS POSITIONED BETWEEN THE SKIN AND THE LUMBAR FASCIA OF A PATIENT

[75] Inventor: Parviz Kambin, Devon, Pa.

[73] Assignee: Smith & Nephew Richards, Inc., Memphis, Tenn.

[ * ] Notice: The portion of the term of this patent subsequent to Sep. 7, 2010, has been disclaimed.

[21] Appl. No.: 88,132

[22] Filed: Jul. 7, 1993

Related U.S. Application Data

[63] Continuation-in-part of Ser. No. 16,681, Mar. 26, 1993, and a continuation-in-part of 965,346, Oct. 23, 1992, which are continuation-in-part of Pat. No. 5,242,443.

[51] Int. Cl.⁶ ..................................... A61F 2/44
[52] U.S. Cl. .............. 623/17; 128/898; 606/61; 606/60
[58] Field of Search .......................... 606/60, 61, 69–75, 606/105; 623/16, 17; 128/898

[56] References Cited

U.S. PATENT DOCUMENTS

| | | |
|---|---|---|
| 1,960,892 | 5/1934 | Boever . |
| 2,501,978 | 3/1950 | Wichman . |
| 2,774,350 | 12/1956 | Cleveland . |
| 3,693,616 | 9/1972 | Roaf . |
| 3,848,601 | 11/1974 | Ma et al. . |
| 3,892,232 | 7/1975 | Neufeld . |
| 3,997,138 | 12/1976 | Crock . |
| 4,341,206 | 7/1982 | Perrett et al. . |
| 4,488,543 | 12/1984 | Tornier . |
| 4,545,374 | 10/1985 | Jacobson . |
| 4,573,448 | 3/1986 | Kambin . |
| 4,653,481 | 3/1987 | Howland . |
| 4,678,459 | 7/1987 | Onik et al. . |
| 4,736,738 | 4/1988 | Lipovsek et al. . |
| 4,743,260 | 5/1988 | Burton . |

(List continued on next page.)

FOREIGN PATENT DOCUMENTS

| | | |
|---|---|---|
| 0159007 | 4/1985 | European Pat. Off. . |
| 3711091A1 | 4/1987 | Germany . |

OTHER PUBLICATIONS

P. Kambin, Arthoscopic Microdiscetomy, 1991, pp. 117–121.
H–H Leu et al, *Ibid*, pp. 123–125.
J. A. N. Shepperd, *Ibid*, pp. 127–129.
P. Kambin, J. Bone and Joint Therapy, 48–A, No. 4, 1966, pp. 779–782.
D. W. Guyer et al, Surgical Rounds for Orthopedics, Feb. 1989, pp. 17–21.
G. Karistrom et al, Cont. Orth., vol. 20, No. 3, Mar. 1990, pp. 285–300.
R. B. Cloward, Clin. Orth. Rel. Res., 193, Mar. 1985, pp. 5–15.
R. Roy–Camille, Clin. Orth. Rel. Res., 203, Feb. 1986, pp. 7–17.
R. Louis, *Ibid*, pp. 18–33.
A. D. Steffer et al, *Ibid*, pp. 45–53.

*Primary Examiner*—Randall L. Green
*Assistant Examiner*—Rob Clarke
*Attorney, Agent, or Firm*—Pravel, Hewitt, Kimball & Krieger

[57] ABSTRACT

A method for vertebral fixation of a pair of vertebrae of a patient, which includes in steps of posterolaterally entering the back of a patient by means of an open surgical technique, introducing a plurality of pedicle screws into the medullary canal of the pedicles of adjacent thoracic and/or lumbar vertebrae or the pedicles of the L5 and S1 vertebrae, to a position where the proximal end lies adjacent the fascia of the patient; inserting pedicle screw linkages between the skin of the patient and the lumbar fascia of the patient and detachably securing the linkage means to the proximal ends of the screws on the same side of the spinous processes of the vertebrae to restrict relative movement between the vertebrae.

42 Claims, 7 Drawing Sheets

U.S. PATENT DOCUMENTS

| | | |
|---|---|---|
| 4,805,602 | 2/1989 | Puno . |
| 4,863,476 | 9/1989 | Shepperd . |
| 4,878,915 | 11/1989 | Brantigan . |
| 4,887,596 | 12/1989 | Sherman . |
| 4,946,458 | 8/1990 | Harms. |
| 5,015,255 | 5/1991 | Kuslich . |
| 5,019,081 | 5/1991 | Watanabe . |
| 5,024,213 | 6/1991 | Asher et al. . |
| 5,026,373 | 6/1991 | Ray et al. . |
| 5,092,866 | 3/1992 | Breard et al. . |
| 5,092,868 | 3/1992 | Mehdian . |
| 5,092,893 | 3/1992 | Smith . |
| 5,129,899 | 7/1992 | Small et al. . |
| 5,129,900 | 7/1992 | Asher et al. . |
| 5,171,279 | 12/1992 | Mathews . |
| 5,176,679 | 1/1993 | Lin . |
| 5,196,015 | 3/1993 | Neubardt . |
| 5,234,431 | 8/1993 | Keller . |
| 5,242,443 | 9/1993 | Kambin . |

OPEN SURGICAL TECHNIQUE FOR VERTEBRAL FIXATION WITH SUBCUTANEOUS FIXATORS POSITIONED BETWEEN THE SKIN AND THE LUMBAR FASCIA OF A PATIENT

This is a continuation-in-part of U.S. patent application Ser. No. 016,681 filed Mar. 26, 1993 and U.S. patent application Ser. No. 965,346 filed Oct. 23, 1992, which are a continuation-in-part of U.S. Pat. No. 5,242,443 issued Sep. 7, 1993.

FIELD OF THE INVENTION

The present invention relates to interbody fusion with subcutaneous internal fixators. More particularly, the present invention relates to a method that allows for the fixation of lumbar vertebrae with subcutaneous internal fixators positioned between the skin and the lumbar fascia of a patient by means of an open surgical technique.

BACKGROUND OF THE INVENTION

The use of internal fixators for fixation of unstable fractures of the vertebrae is known. Also known is a system for internal fixation of vertebrae after the removal of one or more intervertebral discs. External fixation systems for the stabilization of thoracic and lumbar fractures have also been proposed.

The use of existing internal fixators requires a large incision in the back and dissection of the paraspinal muscles, which is a highly invasive procedure. If the internal fixators must be removed, a second major invasive procedure is required. Moreover, patients undergoing an internal fixation procedure require a lengthy rehabilitation, including reconditioning of the muscles.

The use of external fixators requires the patient to carry a fixation assembly on the surface of the back, which is difficult from a physical and psychological point of view for a majority of patients. Moreover, the rehabilitation of paraplegic patients with external fixators has proven to be difficult.

In addition, external fixators have portals in the skin which become sites for infection.

There is thus a need in the art for skeletal fixation that can be performed with minimal injury to the muscular ligamentous structures.

There is also a need in the art for a method of skeletal fixation whereby the extraction of the fixators is accomplished with minimal surgical intervention.

There is a further need in the art for a method of skeletal fixation which is acceptable both psychologically and cosmetically, and which minimizes infection.

SUMMARY OF THE INVENTION

The present invention provides a method for percutaneous fixation of vertebrae of a patient. The method comprises posterolaterally entering the back of a patient percutaneously with a plurality of pedicle screws, screwing each pedicle screw into the medullary canal of the pedicles of adjacent thoracic and/or lumbar vertebrae or the pedicles of the L5 and S1 vertebrae, to a position where the proximal ends of the screws lie adjacent the fascia of the patient; inserting first and second pedicle screw linkage means under the skin of the back of the patient and detachably securing the linkage means to the proximal ends of said screws on the same side of the spinous processes of said vertebrae to restrict relative movement between the vertebrae.

As can be seen, the method of the present invention requires only a small incision to enable the surgeon to link the pedicle screws together. The fixators are located internally, thereby avoiding the disadvantages of external fixation. Since the subcutaneous fixators used in the present invention may be removed routinely after a period of rehabilitation, such as from 10 to 12 weeks, future MRI and CT visualization of the spinal canal and the lateral recesses are then possible. In contrast, the permanent implantation of internal fixators prevents the use of MRI and CT visualizations.

An alternate embodiment of the present invention provides for both a straight and an offset adaptor for use when a pedicle screw and the linkage means do not properly align. An additional embodiment of the present invention provides for an offset bone bolt to be used with the straight adaptor as a replacement for a pedicle screw and the offset adaptor. The offset bone bolt may also be used with external and deeply implanted internal fixation methods.

Another alternate embodiment of the present invention provides a method that allows for the fixation of lumbar vertebrae with subcutaneous internal fixators positioned between the skin and the lumbar fascia of a patient by means of an open surgical technique.

The present invention further provides a kit for percutaneous fixation of vertebrae of a patient, comprising a plurality of pedicle screws and/or offset bolts of different sizes, yet of a size to enable the distal end of each screw or bolt to be screwed into the medullary canal of each pedicle of a vertebra with the proximal end thereof lying adjacent the fascia of a patient. The kit may include a plurality of linkage means proportioned to lie under the skin of the patient and operable to detachably link together the proximal ends of the pedicle screws inserted into the pedicles of the vertebrae.

BRIEF DESCRIPTION OF THE DRAWINGS

The present invention is illustrated in terms of its preferred embodiments in the accompanying drawings in which.

DETAILED DESCRIPTION OF PREFERRED EMBODIMENT

Figure 1:
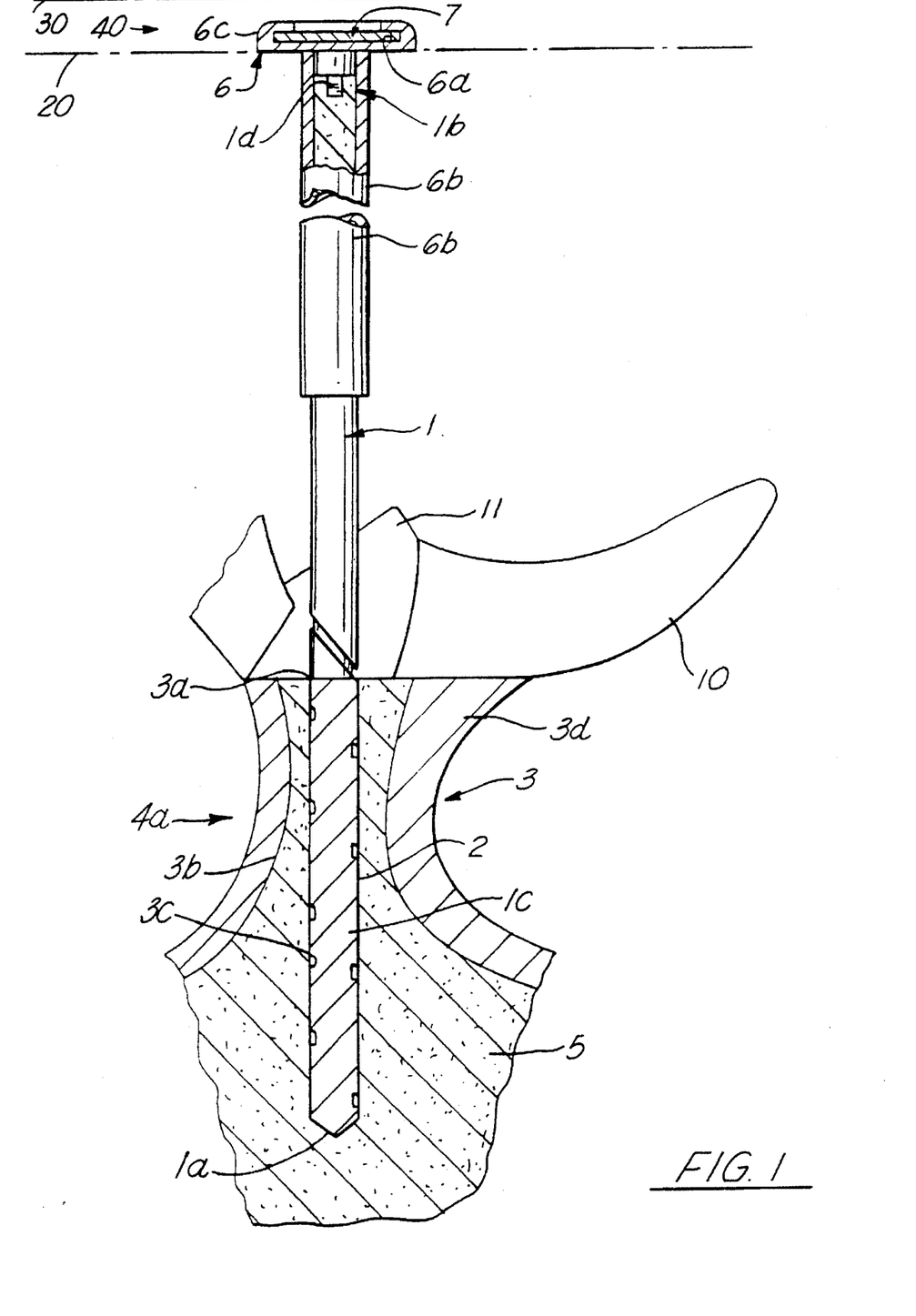
FIG. 1 is a schematic view, partly in section in enlarged scale, of one of the pedicles of a lumbar vertebra into which has been inserted a pedicle screw with a beam member detachably linked to the pedicle screw.

FIG. 1 schematically shows a pedicle screw 1 inserted into the medullary canal 2 of the pedicle 3 of a lumbar vertebra 4 of a patient. The distal end 1a of the pedicle screw 1 extends into the body 5 of the vertebra 4, while the proximal end 1b lies adjacent to the lumbar fascia 20 (shown in phantom line). Fastened to the proximal end 1b of pedicle screw 1 is an adaptor 6 having a slot 6a therein for receiving a beam member 7, here shown in the form of a plate. FIG. 1 shows the pedicle screw 1 inserted into the pedicle 3 situated to one side of the spinous process (not shown) of the vertebra 4. In the same manner, the pedicle (not shown) lying on the other side of the spinous process is also provided with a pedicle screw and an adaptor. The intervertebral disc to be removed lies between the vertebra 4 shown in FIG. 1 and a lumbar vertebra adjacent thereto (FIG. 2), which is also provided with pedicle screws inserted in the pedicles thereof, adaptors fastened to the proximal ends of the pedicle screws, and a beam member in the same manner as shown in FIG. 1.

Figure 2:
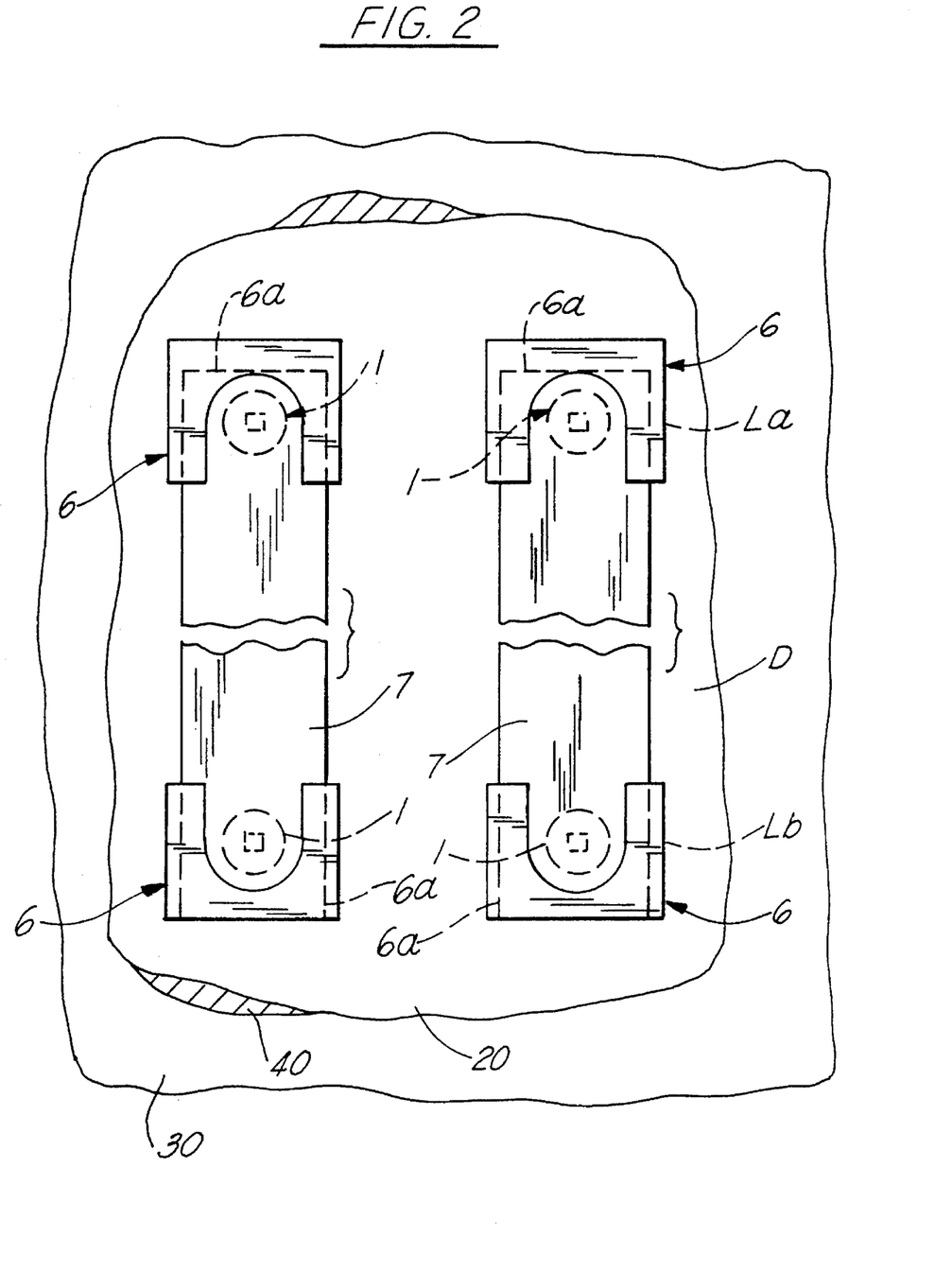
FIG. 2 is a schematic view, in enlarged scale, showing the subcutaneous fixation system of the present invention implanted in a patient.

FIG. 2 is a schematic view of the assembly of pedicle screws, adaptors and beam members of the invention, as viewed posteriorly with part of the skin 30 and subcutaneous tissue 40 of the patient removed for ease of illustration. Thus, pedicle screws 1 are held in the one pair of the pedicles (not shown) of lumbar vertebra La, while the other pair of pedicle screws 1 is held in the pedicle of vertebra Lb immediately above or below lumbar vertebra La. The intervertebral disc D to be removed is between lumbar vertebra La and Lb as schematically indicated. All of the adaptors 6 are preferably flush against the lumbar fascia 20 as shown in FIG. 1. Pedicle screws 1, adaptors 6, and beam members 7 are all made of biocompatable material, suitably stainless steel.

Figure 3:
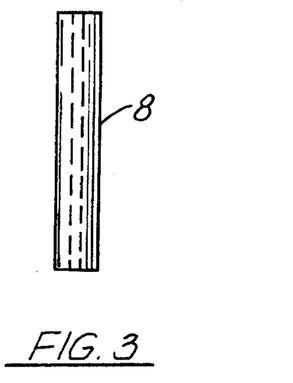
FIG. 3 is an elevational view of a first instrument used to perform the surgical procedure of the present invention.
Figure 4:
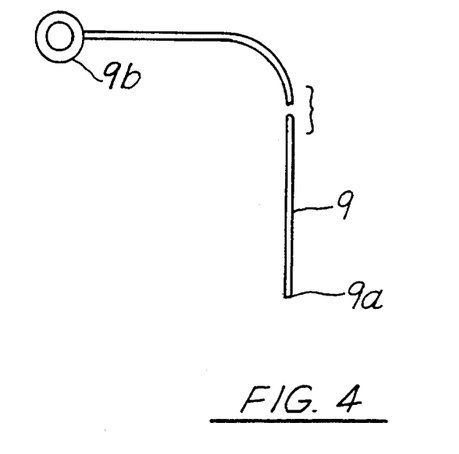
FIG. 4 is an elevational view of a second instrument used to perform the surgical procedure of the present invention.
Figure 5:
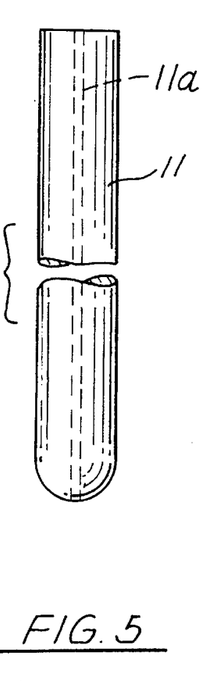
FIG. 5 is an elevational view of a third instrument used to perform the surgical procedure of the present invention.
Figure 6:
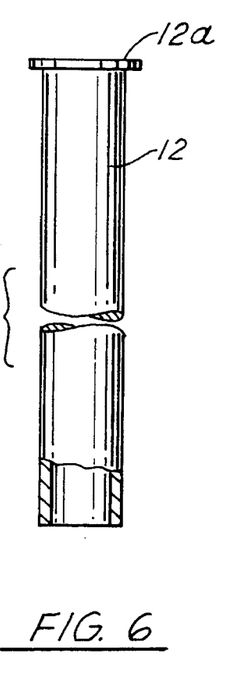
FIG. 6 is an elevational view of a fourth instrument used to perform the surgical procedure of the present invention.

The surgical procedure for percutaneous fixation of lumbar vertebra of the invention may be carried out as follows. The patient is placed prone on a radiolucent table and frame (not shown). The C-arm of a conventional fluoroscope is positioned for anteroposterior visualization of the lumbar vertebrae and the table is tilted away from the C-arm to permit better localization of the pedicles. A cannulated tubular guide 8 (FIG. 3) is maneuvered by hand or by the flexible holder 9 (FIG. 4) having its proximal end 9a secured to the table and carrying at its distal end a ring 9b for holding guide 8. The guide 8 is maneuvered with the holder 9 until the guide 8 is aligned with the longitudinal axis of the pedicle, after which the holder 9 is locked into place. When properly aligned, the guide 8 will appear by fluoroscopy as an opaque circle in the center of the pedicle. A guide wire (not shown), suitably of 2 mm outside diameter, is introduced into the guide 8 and is advanced through the skin of the patient's back, posterolaterally toward the pedicle 3. The guide wire is tapped with a mallet into the cortical bone at the junction of the base of the transverse process 10 (FIG. 1) and the proximal articular process 11. After removal of guide 8, a cannulated obturator 11 (FIG. 5) having a lumen 11a is placed over the guide wire and advanced through the skin of the patient's back to the pedicle 3, followed by placing an access cannula 12 (FIG. 6) over the obturator 11, and advancing the cannula 12 to the pedicle 3.

Figure 7:
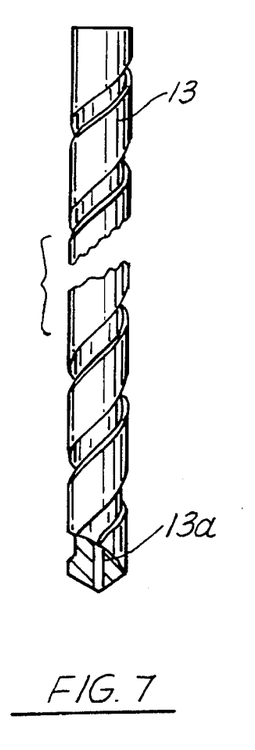
FIG. 7 is an elevational view of a fifth instrument used to perform the surgical procedure of the present invention.
Figure 8:
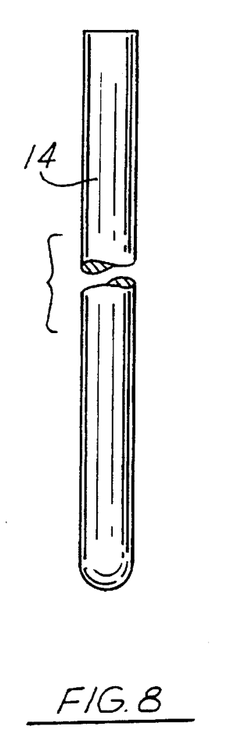
FIG. 8 is an elevational view of a sixth instrument used to perform the surgical procedure of the present invention.

The obturator 11 is then removed, and a cannulated drill 13 having a lumen 13a (FIG. 7) is placed over the guide wire and advanced to the pedicle 3. By manually operating the drill 13, the opening of the cortex of the pedicle is enlarged to form an entrance 3a (FIG. 1) into the medullary canal 3b of the pedicle 3. The cannulated drill 13 is removed and a blunt end pedicle screw probe 14 (FIG. 8) is manually advanced into the medullary canal 3b with a twisting motion, to crush the cancellous bone of the medullary canal 3b thus creating a tunnel or bore 3c (FIG. 1) extending from the pedicle 3 into the vertebral body 5 (FIG. 1). The probe 14 or a blunt end K-wire can be inserted into the bore 3c, the position and length of the probe or K-wire being checked by anteroposterior and lateral fluoroscopy.

If desired by the surgeon, the bore 3c may be tapped to receive the threads 1c of the pedicle screw 1. Alternatively, a self-tapping pedicle screw may be used. Before implanting the pedicle screw 1, the bore 3c may be inspected arthroscopically to make certain that the cortex 3d (FIG. 1) of the pedicle 3 has not been violated; if it has been, the surgeon may abort the procedure.

The length of the pedicle screw 1 to be used may be determined by the use of a K-wire. Thus, the K-wire can be used to measure the depth of bore 3c, and the distance between the bone and the lumbar fascia 20.

Figure 9:
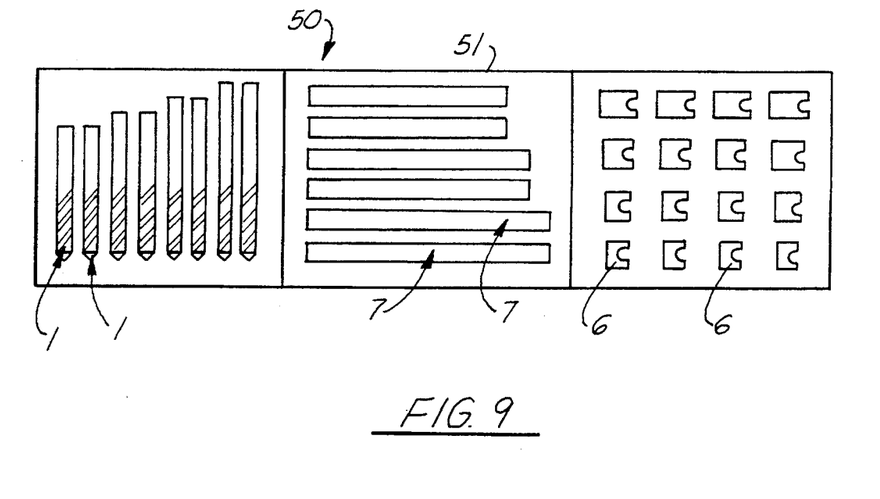
FIG. 9 is a plan view of a kit for carrying out the method of the present invention.

The appropriate pedicle screw 1 is selected from the kit 50 (FIG. 9) containing a plurality of pedicle screws 1, beam members 7 and adaptors 6 in a container 51. The pedicle screws 1 are all of a size to enable the distal end 1a of each screw 1 to be screwed into the medullary canal 3b of the pedicle 3 of a lumber vertebrae with the proximal end 1b thereof lying adjacent the lumbar fascia 20 of a patient, while the beam members 7 are proportioned to lie under the skin 30 of the patient and operate to detachably link together the proximal ends 1b of a pair of pedicle screws 1 (FIG. 2) inserted into the pedicles 3 of the lumbar vertebrae.

Generally, the pedicle screws 1 in kit 50 will be of different lengths and diameters. However, it is contemplated that the kit may contain pedicle screws 1 of different lengths and the same diameters. Moreover, while the beam members 7 may be of different lengths, all are sized to be received in adaptors 6, and since some beam members 7 in the kit 51 may be much longer, they can be cut to length by the surgeon. Adaptors 6 will comprise adaptors having a slot 6a open at one end and closed at the other, such as the upper adaptors 6 as viewed in FIG. 2, while others will have a slot 6a open at both ends, such as the lower adaptors 6 as viewed in FIG. 2.

The pedicle screw 1 selected is placed into the access cannula 12 and thence into the bore 3c. An allen wrench (not shown) may be inserted into the recess 1d (FIG. 1), to drive the pedicle screw 1 into the bore 3c. However, pedicle screw 1 may be provided with any suitable means for engaging a pedicle screw driver, such as a slot in screw 1 and a corresponding blade for the driver.

Figure 10:
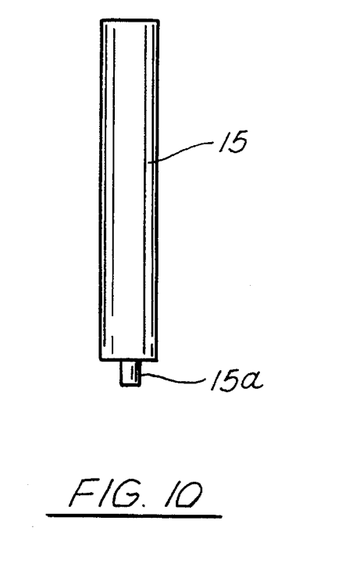
FIG. 10 is an elevational view of a tool used to carry out the method of the present invention.

After pedicle screw 1 is implanted, an adaptor guide 15 (FIG. 10) having an outside diameter smaller than the inside diameter of the tubular body 6b is inserted through the access cannula 12 so that the projection 15a enters recess 1d (FIG. 1), after which the access cannula 12 is removed. An adaptor 6 is slid over the adaptor guide 15 and is screwed in place over the eternal threads on the proximal end 1b of screw 1, to the position shown in FIG. 1. All of the adaptors have an internally threaded tubular body 6b extending from a slotted cap 6c, the slot 6a lying in a plane perpendicular to the tubular body 6b. Adaptor guide 15 may also be used as a driver for the pedicle screws, for example by providing a slot (not shown) in the distal end of guide 15 to receive a cross-bar that serves as a handle.

After the pedicle screws are in place, the disc D is removed by percutaneous total discectomy. See, e.g., U.S. Pat. Nos. 4,573,448, 4,545,374 and 4,678,459. Bone grafts are then packed between the vertebral plates, and the vertebrae are aligned into their desired position by compression, extension and/or angulation using a wrench (not shown) or other tool that securely grasps the proximal ends 1b of the screws and/or the adaptors 6.

When the vertebrae are properly aligned, they are locked in place by inserting the beam members 7 into the adaptors 6 and, in turn, locking the beam members 7 in place. Thus, one end of the beam member 7 is received in an adaptor 6 having a slot 6a open at one end and closed at the other, such as the upper adaptors 6 shown in FIG. 2, while the other end is received in an adaptor 6 having a slot open at both ends, such as the lower adaptors 6 shown in FIG. 2.

To insert the beam member 7 into the adaptors 6, a small incision (not shown), may, if necessary, be made in the patient's back adjacent the adaptors 6 having a slot 6a having two open ends. The beam member 7 is inserted into the subcutaneous tissue 40 via the incision and advanced through adaptors 6 until the distal end of the beam member 7 contacts the closed end of adaptors 6. If necessary, the beam members 7 may be bent to allow the beam member 7 to be received by the adaptors 6. Each beam member 7 is locked in place in adaptors 6 by set screws (not shown) or by crimping the adaptors 6 and the ends of the beam member 7 or by any other suitable detachable locking means. The incision is then closed.

Suitably, the guide wire may be about 10 to 12 inches long while the cannulated obturator 11 may be about 6 to 7 inches long and about 7 mm in diameter, with a lumen 11a sized to slide over the guide wire. The access cannula 12 may be about 5 to 6 inches long with an inside diameter of about 7 mm. The cannulated drill 13 also has a lumen 13a sized to slide over the guide wire and will have an outside diameter somewhat smaller than the outside diameter of the pedicle screw.

The pedicle screw 1 may have an outside diameter of about 5 to 6.5 mm and may suitably be from about 45 to about 70 mm in total length, with a distal portion 1c of about 20 to about 45 mm carrying a bone screw in thread form and the proximal portion being threaded to receive the adaptor 6. The tubular body 6b of the adaptor 6 may be about 15 to about 30 mm long, with a cap 6c of about 30×30 mm square and about 4 to 10 mm thick. The slot 6a must accommodate the beam member 7. Plates of about 5 to about 10 mm wide by about 35 to about 90 mm long are suitable, the thickness of the plates 7 being about 2 to 5 mm. Rods 16 of about 5 to about 7 mm in diameter and 35 to about 90 mm long are also suitable. Anatomical variations of a particular patient may require the use of different dimensions.

Figure 11:
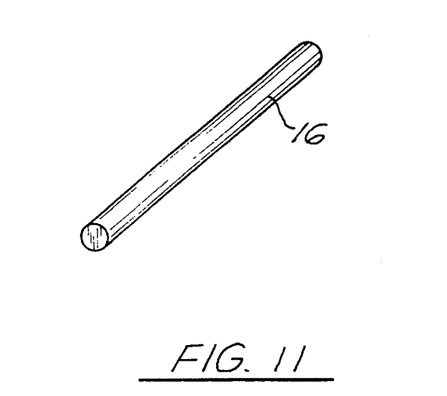
FIG. 11 is a view in perspective of an alternative embodiment of the present invention.
Figure 11A:
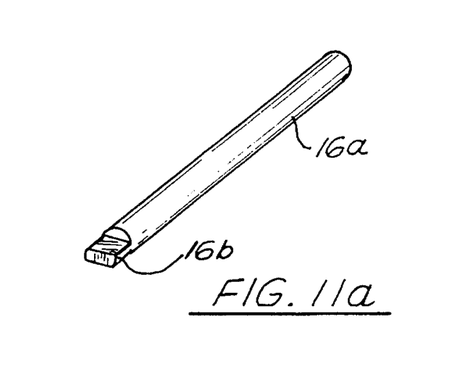
FIG. 11a is a view in perspective of an alternative embodiment of the present invention.

It is presently preferred that the adaptor cap 6 have a low profile, i.e. with a small thickness relative to its length and width. Preferably the cap 6c has a substantially flat top and flat underside as shown, but other configurations may be used as long as the cap 6 is proportioned to lie beneath the skin and/or the lumbar fascia 20. Thus, if the beam members 7 are in the form of rods 16 (FIG. 11), the cap 6 may still be flat but a suitable cylindrical slot (not shown) will be used. Alternatively, a rod 16a with a flat end 16b, as shown in FIG. 11a, can be used with the cap 6 on one end and an cap 6 having a suitable cylindrical slot (not shown) for the round end of rod 16.

There may be situations in which a percutaneous procedure for performing a discectomy or other spinal operation is not indicated. This situation presents itself, for example, when a patient has disc herniation associated with segmental instability, or central stenosis, or spondyloisthosis which requires excision of the posterior arch or decompression of the pars interarticularis. When a patient is presented with these complications, an open surgical technique may be preferred and the subcutaneous fixators, described above for use with a percutaneous procedure, can also be used in such an open procedure.

Vertebral fixation with subcutaneous fixators positioned between the skin 30 and the lumbar fascia 20 of a patient can be used in any type of laminectomy procedure, such as for example, decompression of the spinal disc, discectomy, bone grafting procedures or vertebral fusion. A total discectomy and fusion using an open surgical procedure in which the fixation of the vertebrae is accomplished by this method can be carried out as follows.

The patient is placed prone on a radiolucent table and frame (not shown). A posterior medial or mid-line incision is made in the back of the patient. The skin 30 is retracted, and the spinal processes and laminae of the vertebrae adjacent to the fusion site are exposed and the paravertebral muscles are retracted. A partial or complete facetectomy may be performed if considered necessary. The disc D is removed utilizing a known discectomy procedure and allograft bone is inserted in the space remaining between the vertebrae after the disc D has been removed. The allograph can be inserted through the laminotomy side or through a posterolateral approach. Chipped cancellous or cortical autologous grafts are then packed between the cancellous bone of the vertebrae above and below the discectomy site.

The skin 30 is retracted under fluoroscopic control and four guide pins or wires (not shown) are inserted into the pedicles of the segments adjacent to the fusion site. A small incision is made into the fascia 20 adjacent to the guide wires. The cannulated obturator 11 (FIG. 5) having a lumen 11a is placed over the guide wire and advanced through the tissue to the pedicle 3, followed by placing the access cannula 12 (FIG. 6) over the obturator 11, and advancing the cannula 12 to the pedicle 3.

The obturator 11 is then removed, and a cannulated drill 13 having a lumen 13a (FIG. 7) is placed over the guide wire and advanced to the pedicle 3. By manually operating the drill 13, the opening of the cortex of the pedicle is enlarged to form an entrance 3a (FIG. 1) into the medullary canal 3b of the pedicle 3. The cannulated drill 13 is removed and a blunt end pedicle screw probe 14 (FIG. 8) is manually advanced into the medullary canal 3b with a twisting motion, to crush the cancellous bone of the medullary canal 3b thus creating a tunnel or bore 3c (FIG. 1) extending from the pedicle 3 into the vertebral body 5 (FIG. 1). A blunt end K-wire can be inserted into the bore 3c, the position and length of the K-wire being checked by anteroposterior and lateral fluoroscopy.

If desired by the surgeon, the bore 3c may be tapped to receive the threads 1c of the pedicle screw 1. Alternatively, a self-tapping pedicle screw may be used. The length of the pedicle screw 1 to be used may be determined by the use of the K-wire. Thus, the K-wire can be used to measure the depth of bore 3c, and the distance between the bone and the lumbar fascia 20.

The appropriate pedicle screw 1 is selected from the kit 50 (FIG. 9) containing a plurality of pedicle screws 1, beam members 7 and adaptors 6 in a container 51. The pedicle screws 1 are all of a size to enable the distal end 1a of each screw 1 to be screwed into the medullary canal 3b of the pedicle 3 of a lumbar vertebrae with a proximal end 1b thereof lying adjacent the lumbar fascia 20 of a patient, while the beam members 7 are proportioned to lie under the skin 30 of the patient and operate to detachably link together the proximal ends 1b of a pair of pedicle screws 1 (FIG. 2) inserted into the pedicles 3 of the lumbar vertebrae.

After a pedicle screw 1 is selected, it is placed in the bore 3c. An allen wrench (not shown) is inserted into the recess 1d (FIG. 1), to drive the pedicle screw 1 into the bore 3c. However, the pedicle screw 1 may be provided with any other suitable means for engaging a pedicle screw driver, such as a slot for receiving the corresponding blade for the driver.

After the pedicle screws are implanted, an adaptor 6 is screwed in place over the external threads on the proximal end 1b of the pedicle screw 1, to the position shown in FIG. 1. All of the adaptors have an internally threaded tubular body 6b extending from a slotted cap 6c, and the slot 6a lies on a plane perpendicular to the tubular body 6b.

The incision into the fascia 20 is closed and the beam members 7 are positioned such that they lie under the skin 30 but over the fascia 20. The beam members 7 are inserted into the adaptors 6 and, in turn, locking the beam members 7 in place. Thus, one end of the beam member 7 is received in an adaptor 6 having a slot 6a open at one end and closed at the other, such as the upper adaptor 6 shown in FIG. 2, while the other end is received in an adaptor 6 having a slot open at both ends, such as the lower adaptors 6 shown in FIG. 2. Each beam member 7 is locked in place in adaptor 6 by set screws (not shown) or by crimping the adaptor 6 in the ends of the beam member 7 or by other suitable detachable locking means. The mid-line incision is then closed.

When a situation presents itself where the transverse processes are exposed through a separate paramedial longitudinal incision through the fascia 20, such as when a posterolateral intertransverse fusion is desired, the pedicle screws 1 can be inserted under direct vision and fluoroscopic control without the use of access cannulas. This method of insertion can be carried out as follows.

After the paramedial longitudinal incision is made, a guide wire (not shown) is placed in the pedicle 3 and the correct position of the guide wire is confirmed fluoroscopically (not shown). The medullary canal 3b of the pedicle 3 is tapped with cannulated screw taps (not shown), preferably using taps of a smaller diameter than the diameter of the pedicle screw 1 selected. For example, for a 7 mm pedicle screw 1, a 6.4 mm screw tap is used. Before implanting the pedicle screw 1, the medullary canal 3b of the pedicle 3 may be examined to make certain that the cortex 3d (FIG. 1) of the pedicle 3 has not been violated.

The appropriate pedicle screw 1 is selected from the kit 50 (FIG. 9) containing a plurality of pedicle screws 1, beam members 7 and adaptors 6 in a container 51. The pedicle screws 1 are all of a size to enable the distal end 1a of each screw 1 to be screwed into the medullary canal 3b of the pedicle 3 of a lumber vertebrae with the proximal end 1b thereof lying adjacent the lumbar fascia 20 of a patient, while the beam members 7 are proportioned to lie under the skin 30 of the patient and operate to detachably link together the proximal ends 1b of a pair of pedicle screws 1 (FIG. 2) inserted into the pedicles 3 of the lumbar vertebrae.

After a pedicle screw 1 is selected, it is placed in the bore 3c. An allen wrench (not shown) is inserted into the recess 1d (FIG. 1), to drive the pedicle screw 1 into the bore 3c. However, the pedicle screw 1 may be provided with any other suitable means for engaging a pedicle screw driver, such as a slot for receiving the corresponding blade for the driver.

After the pedicle screws are implanted, an adaptor 6 is screwed in place over the external threads on the proximal end 1b of the pedicle screw 1, to the position shown in FIG. 1. All of the adaptors have an internally threaded tubular body 6b extending from a slotted cap 6c, and the slot 6a lies on a plane perpendicular to the tubular body 6b.

The incision in the fascia 20 is closed and the beam members 7 are positioned such that they lie under the skin 30 but over the fascia 20 (FIG. 1). The beam members 7 are inserted into the adaptors 6 and, in turn, locking the beam members 7 in place. Thus, one end of the beam member 7 is received in an adaptor 6 having a slot 6a open at one end and closed at the other, such as the upper adaptor 6 shown in FIG. 2, while the other end is received in an adaptor 6 having a slot open at both ends, such as the lower adaptors 6 shown in FIG. 2. Each beam member 7 is locked in place in adaptor 6 by set screws (not shown) or by crimping the adaptor 6 in the ends of the beam member 7 or by other suitable detachable locking means. The mid-line incision is then closed.

Figure 12:
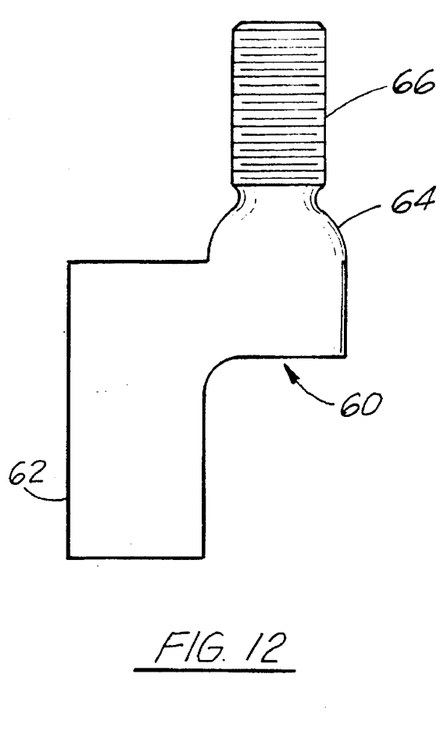
FIG. 12 is an elevational view of an alternative embodiment of the present invention.
Figure 13:
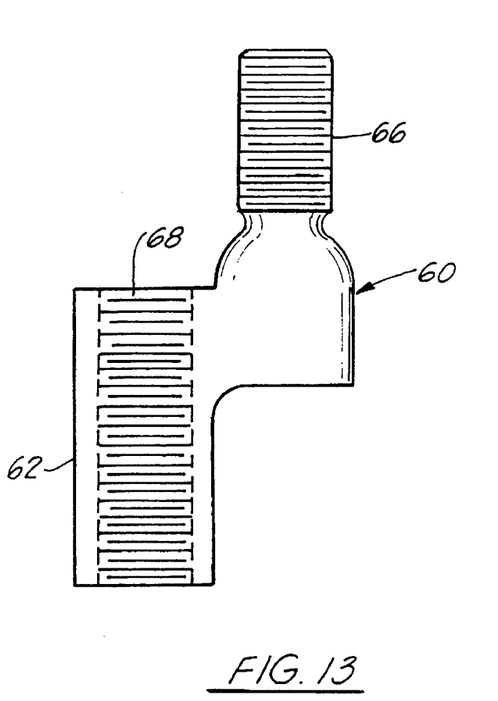
FIG. 13 is a partial sectional view of the alternative embodiment shown in FIG. 12.
Figures 15, 16, 21:
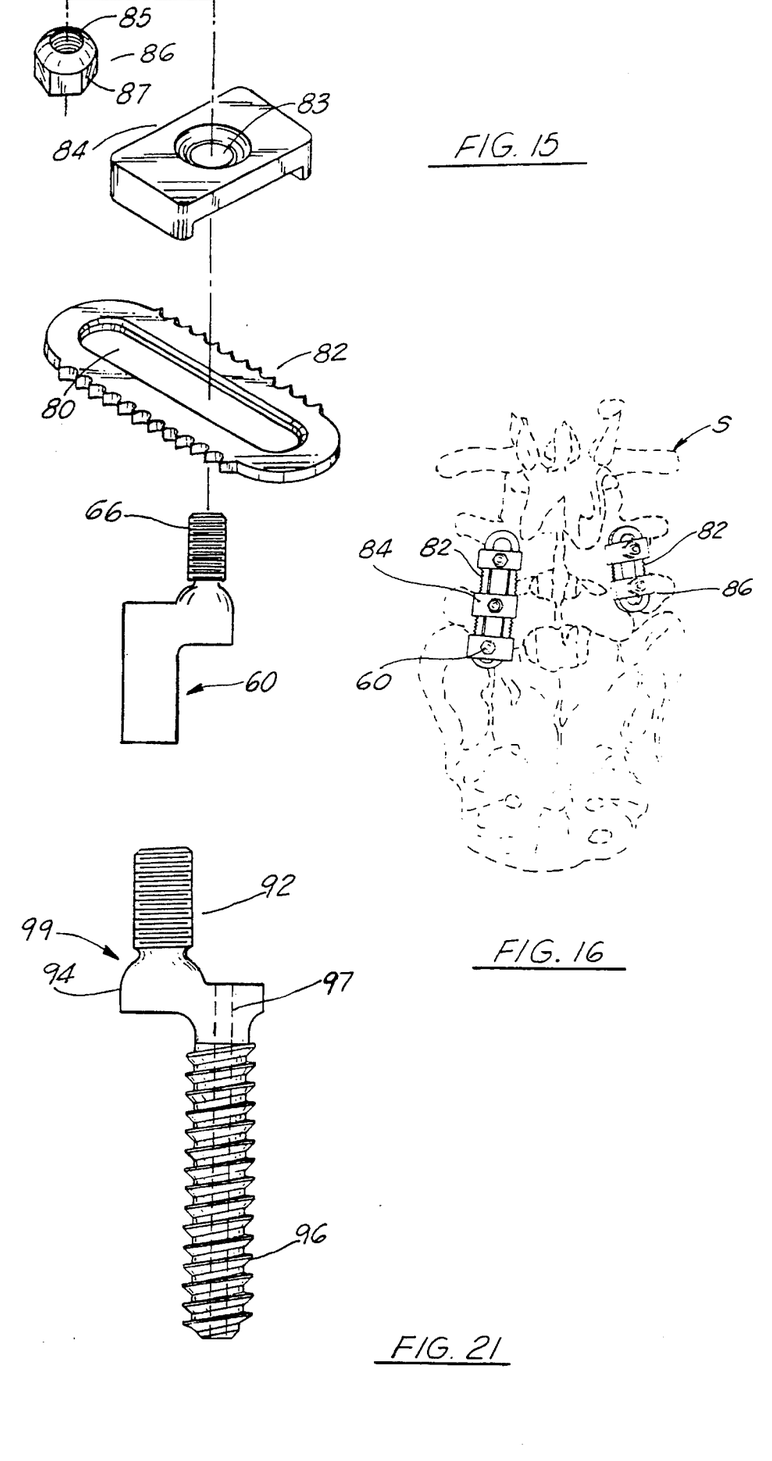
FIG. 15 is a perspective exploded view of an alternative linkage system.
FIG. 16 is a schematic view illustrating an alternate embodiment of the present invention in use as part of a spinal fixation system.
FIG. 21 is a partial sectional view of a forth alternate embodiment of the present invention.

After the pedicle screws are in place, in any of the above-described procedures, the proximal end 1b of each pedicle screw 1 may not align in a position that allows the beam member 7 to lock in place. Additionally, if the pedicle screw 1 is implanted at an angle into the body 5 of the vertebrae 4 the proximal end 1b of each pedicle screw 1 may touch or be too close together to allow the beam member 7 to lock into place. In these situations an alternative to the adaptor 6 is desirable to allow for easier insertion of the beam member 7. An alternative embodiment of the adaptor 6 is an offset adaptor 60, as shown in FIG. 12. The offset adaptor 60 is an internally threaded tubular body 62 having an offset upper end portion 64 with fine threads 66. FIG. 13 illustrates the internal threading 68 of the tubular body 62, which is designed to engage with the external threads on the proximal end 1b of the pedicle screw 1. As shown in FIG. 15, the offset adaptor 60 can be used with an alternate linkage system such as a plate 82, a washer 84, and a nut 86 described and shown in U.S. Pat. No. 5,129,899 which is hereby fully incorporated by reference. The plate 82 has upper and lower surfaces and parallel opposed outer edges with an elongated slot 80 along the central longitudinal axis of the plate 82 with the slot 80 being surrounded by a peripheral portion having the parallel opposed outer edges. The edges have fine adjustment means in the form of teeth or groves that extend between the upper and lower surfaces of the plate 82 for defining various fine adjustment positions of the bone bolt 90 with respect to the plate 82. The washer 84 interfaces with the plate 82 and the bone bolt 90 and has a side portion for engaging the fine adjustment means at the outer edges of the plate 82. The fine adjustment means determine the position of the bone bolt 90 with respect to the plate 82.

Figure 19:
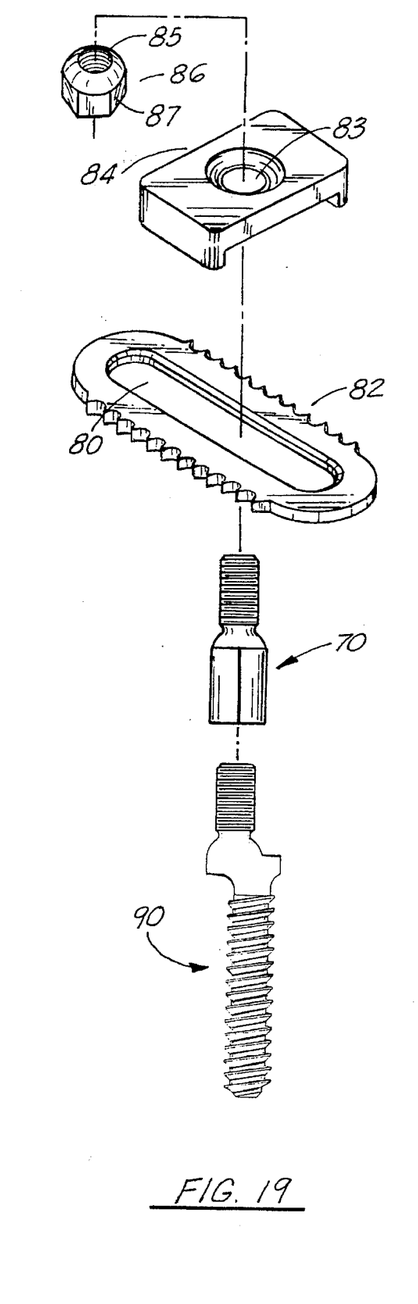
FIG. 19 is a perspective exploded view of an alternate linkage system.

The washer 84 has an opening 83 for placement of the proximal end 92 of the bone bolt 90, with the opening 83 having a countersunk portion for receiving a nut. The nut 86 has a longitudinally extending shaped portion 87 that fits the washer 84 at the countersunk opening 83. The nut 86 includes internal threads 85 for cooperation with the fine threads of a bone bolt or adaptor 60 (FIG. 15) or 70 (FIG. 19).

When an alternate linkage system as shown in FIG. 15 is used, the plate 82 is placed over the upwardly projecting screw portion 66 of the offset adaptor 60. The washer 84 is placed over the plate 82 and is secured by the nut 86 that engages the threaded screw portion 66 of the offset adaptor 60. The offset adaptor 60 can be of varying lengths to accommodate the distance between the proximal end 1b of the pedicle screw 1 and the lumbar fascia 20 of the patient. FIG. 16 illustrates a pair of spaced apart plates 82 with the attachment of the offset adaptor 60, the washer 84, and the nut 86 as part of an implanted, overall spinal fixation system.

Figure 14:
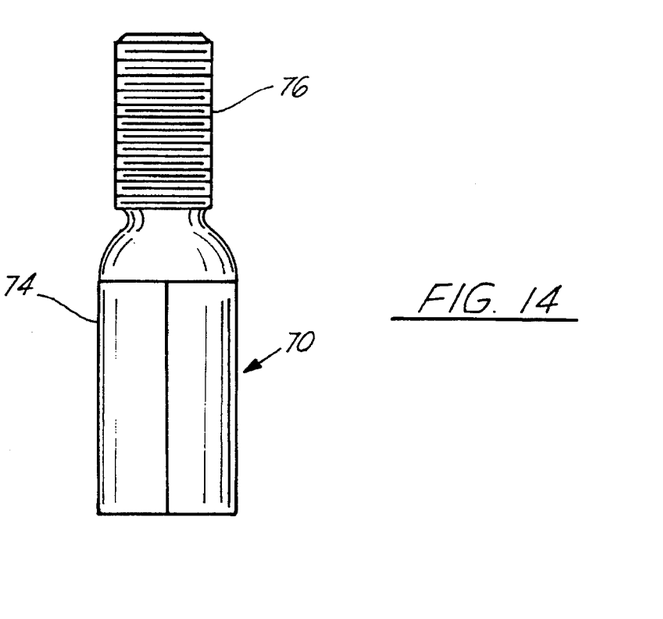
FIG. 14 is an elevational view of a second alternative embodiment of the present invention.

When the alternate linkage system of FIG. 15 is used, but there is no need to offset the connection between the pedicle screw 1 and the beam member 7, a second alternate embodiment in the form of straight adaptor 70, as shown in FIG. 14, can be used. The straight adaptor 70 has a finely threaded upper end portion 76 and a body 74 that is generally hexagonal in shape. The threaded upper portion 76 engages with the internal threads 85 of the nut 86. The adaptor 70 has an internally threaded portion for engagement with the external threads on the proximal end 1b of the pedicle screw 1. The straight adaptor 70 can be of varying lengths to accommodate the distance between the proximal end 1b of pedicle screw 1 and the lumbar fascia 20 of the patient. Additionally, both adaptor 60 and 70 could be of a sufficient length to be used with an external fixation system. As with the other elements of the system, the adaptors 60 and 70 may be formed of stainless steel or other biocompatable materials.

Figure 17:
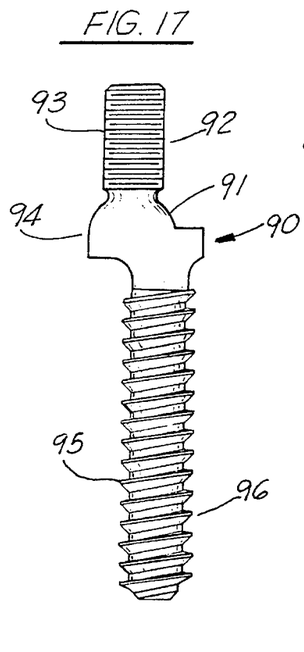
FIG. 17 is an elevational view of a third alternate embodiment of the present invention.
Figure 18:
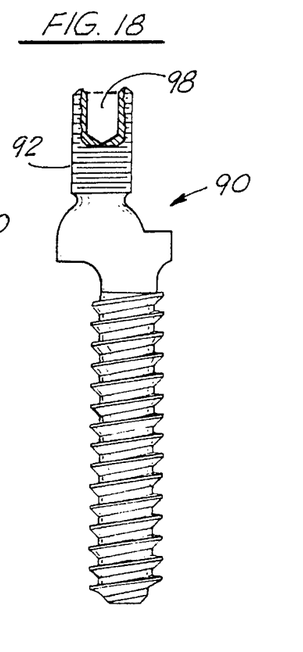
FIG. 18 is a partial sectional view of the alternate embodiment show in FIG. 17.

An alternate fixator to the pedicle screw 1 may be used where, instead of the pedicle screw 1 and the offset adaptor 60, an offset bone bolt 90 and the straight adaptor 70 is used. As shown in FIG. 17, the offset bone bolt 90 has a proximal or upper end portion 92, a middle portion 94 and a distal or lower end portion 96. The middle portion 94 is axially offset from the distal portion 96 and has a load bearing surface 91 for engagement with a linkage system as that illustrated in FIG. 19. The upper end portion 92 of the offset bone bolt 90 has fine threads 93 designed to engage with the internally threaded portion of the adaptor 70 as shown in FIG. 19. The lower end portion 96 has threads 95 typical of those found on bone screws. As shown in FIG. 18, the upper end portion 92 has a recess 98 to accommodate an allen wrench (not shown) or other suitable driver used to implant the offset bone bolt 90 into the pedicle 3 as shown in FIG. 1.

An alternate embodiment of the offset bone bolt 90 is shown in FIG. 21, where an offset bone bolt 99 has a middle portion 94 with a greater offset and the distal portion 96 is cannulated with an aperture 97 extending along the longitudinal axis of the distal portion 96 for allowing a guide wire to extend therethrough. The method of using cannulated bolts or screws with a guide wire is generally described in U.S. Pat. No. 4,790,297.

When an alternate linkage system as shown in FIG. 19 is used, the straight adaptor 70 is placed over the upper end portion 96 of the offset bone bolt 90. The plate 82 is placed over the upwardly projecting portion 76 of the adaptor 70. The washer 84 is placed over the plate 82 and is secured by the nut 86 that engages the threaded screw portion 76 of the adaptor 70.

Figure 20:
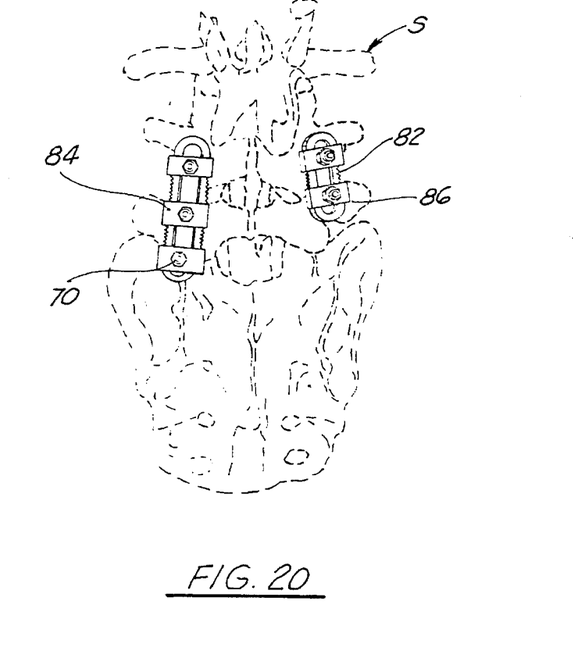
FIG. 20 is a schematic view illustrating the alternate embodiment of FIG. 17 in use as part of a spinal fixation system.

Additionally, the offset bone bolt 90 could be of a length sufficient to be used with an external fixation system or of a length appropriate for a deeply implanted fixation system where the fixation system is adjacent to the vertebrae. If desired, the offset bone bolt 90 may be used with a deeply implanted internal fixation system and a linkage system of the type illustrated in FIG. 19. With a linkage system of this type the plate 82 is placed directly over the upwardly projecting portion 92 of the offset bone bolt 90 so that the portion 92 extends through the slot 80 of the plate 82. The undersurface of the plate 82 rests on the load bearing surface 91 of the middle portion 94 of the bone bolt 90. The washer 84 is placed over the plate 82 in such a manner that the proximal portion 92 of the bone bolt 90 extends through the washer opening 83 and is secured by the nut 86 that engages the threaded upper portion 93 of the offset bone bolt 90. As with other elements of the system, the offset bone bolt 90, the plate 82, washer 84 and nut 86 may be formed of stainless steel or other biocompatible materials. FIG. 20 illustrates a pair of spaced apart plates 82 with the attachment of the straight adaptor 70, the washer 84, and the nut 86 as part of an implanted, overall spinal fixation system.

While the drawings show for convenience the fixation of only two vertebrae, it is to be understood that more than two vertebrae may be fixed. For example, when two intervertebral discs are to be removed, say between vertebrae L1, L2 and L3, pedicle screws 1 will be implanted in the pedicles of the three vertebrae. The pedicle screws rising from the L1 or L3 vertebra will carry an adaptor 6 having a slot closed at one end, while the other pedicle screws will carry an adaptor 6 having a slot open at both ends. A longer beam member 7 is then slid through the adaptors 6 and locked into place as described above. Alternately, when more than two vertebrae are fixed the offset adaptor 60 or the straight adaptor 70 may be used in place of the adaptor 6 as seen in FIG. 16. In any of the above procedures the offset bone bolt 90 and 99 and the adaptor 6 or 70 may be used in place of the pedicle screw 1 and the adaptor 6, 60 or 70. Moreover, the surgeon may elect to fix three vertebrae even if only one disc is to be removed.

While the present invention has been illustrated in the accompanying drawings in terms of the fixation of adjacent lumbar vertebrae, it is to be understood that the same procedures are followed for the fixation of adjacent thoracic vertebrae, of adjacent thoracic and lumbar vertebrae and of the L5 and S1 vertebrae. In each case, the procedure is effected percutaneously as described above. That is, the center of each pedicle to be implanted with a pedicle screw or offset bone bolt is located fluoroscopically and the pedicle screws or offset bone bolts are implanted percutaneously or in an open surgical technique as described above, and the proximal ends of the pedicle screws or offset bone bolts are linked together beneath the skin at or preferably flush with the muscle fascia as described above. If considered desirable by the surgeon, the beam members and/or the pedicle screws or offset bone bolts may be linked transversely such as by the use of 1.5 mm cross-wires.

Moreover, while the kit 50 is illustrated as containing the screws, beam members and adaptors 6, the same or auxiliary kits may be provided with adaptors 60, adaptors 70 and/or offset bone bolts 90 and 99 and the instruments used to carry out the surgical procedure, such as the instruments shown in FIGS. 3–8 and 10.

What is claimed is:

1. A method for fixation of vertebrae of a patient, said patient having a back covered with skin under which is fascia, said patient also having vertebrae with spinous processes and pedicles, said pedicles having medullary canals, said method comprising the steps of:
   a) posterolaterally entering the back of a patient by means of forming an incision with an open surgical technique wherein tissue is retracted and vertebrae are exposed;
   b) introducing a plurality of pedicle screws having proximal ends through a plurality of small incisions into the medullary canal of the pedicles of adjacent vertebrae, to a position where the proximal ends of said pedicle screws lie adjacent the fascia of the patient beneath the skin;
   c) inserting first and second pedicle screw linkage means between the skin of the patient and the fascia of the patient;
   d) detachably securing said linkage means to said proximal ends of said screws on a same side of the spinous process of said vertebrae to restrict relative movement between said vertebrae; and
   e) closing the incisions after the linkage means is secured to the screws.

2. The method according to claim 1, wherein said pedicle screws are implanted in the pedicles of adjacent thoracic vertebrae.

3. The method according to claim 1, wherein said pedicle screws are implanted in the pedicles of adjacent lumbar vertebrae.

4. The method according to claim 1, wherein said pedicle screws are implanted in the pedicles of adjacent thoracic and lumbar vertebrae.

5. The method according to claim 1, wherein said pedicle screws are implanted in the pedicles of the L5 and S1 vertebrae.

6. A method according to claim 1, wherein an adaptor having a tubular body with a threaded offset upper end is provided for each pedicle screw.

7. The method according to claim 6, wherein said tubular body of said adaptor is internally threaded.

8. A method according to claim 1, wherein an offset bone bolt having a distal threaded end configured to be surgically implanted into a patient's bone and an integral axially offset middle portion with a proximal threaded end portion is introduced into the medullary canal of the pedicles.

9. A method according to claim 8, wherein an adaptor having an internally threaded tubular body and a threaded upper end member is provided for each offset bone bolt.

10. A method for fixation of a pair of lumbar vertebrae of a patient, said patient having a back covered with skin under which is fascia, said patient also having lumbar vertebrae with cortical bone, transverse processes, proximal particular processes and pedicles, said pedicles having medullary canals, said method comprising the steps of:
   a) posterolaterally entering the back of a patient by means of forming a first incision with an open surgical technique and performing a laminectomy procedure at the site of the first incision;
   b) forming a second small incision into the fascia of a patient adjacent to the first incision;
   c) forming an opening in the cortical bone of each said pair of lumbar vertebrae at a juncture of a base of the transverse process and the proximal articular process of said vertebrae, said openings in each pair of vertebrae providing entrances into the respective medullary canals of the pedicles supporting said vertebral processes;
   d) subcutaneously screwing into each of said medullary canals a pedicle screw having a proximal end to a position where the proximal end thereof lies adjacent the fascia of the lumbar vertebrae of the patient, providing for each pedicle screw an adapter having a slotted cap and a tubular body extending therefrom; said slotted cap lying in a plane perpendicular to said tubular body;
   e) fastening the tubular body onto the proximal end of each said pedicle screws such that the slotted cap of the adapter lies between the lumbar fascia and skin of the patient;
   f) closing the second incision;
   g) positioning at least one beam member under the skin and onto the slotted caps and detachably locking said beam member into said caps; and
   h) closing the first incision after the beam member is locked into the caps.

11. The method according to claim 10, wherein said vertebrae are aligned before insertion of said beam member, said beam member being locked in place to maintain said alignment.

12. The method according to claim 10, wherein one of the slotted caps has two ends which are open at both ends while the other slotted cap has two ends in which one end is open and the other end is closed, said beam member being slid through said open end of said one cap into said closed end of said other cap.

13. The method according to claim 10, wherein each said opening is formed by locating a selected opening position fluoroscopically, posterolaterally introducing a guide wire through the fascia of a patient's back and advancing said guide wire to said selected position and into said cortical bone at said juncture; sliding a access cannula in the form of a cannulated obturator over said guide wire and advancing said obturator to said juncture; removing said obturator; forming said opening with a pedicle cannulated drill means inserted in said access cannula over said guide wire and thereafter removing said guide wire and said drill means.

14. The method according to claim 10, wherein a blunt end member is inserted in said access cannula and advanced into said medullary canal to crush cancellous bone therein and thereby form a bore in said medullary canal.

15. The method according to claim 14, wherein said pedicle screw is screwed into said medullary canal bore via said access cannula, and said access cannula is removed.

16. The method according to claim 15, wherein said proximal ends of said pedicle screw includes means for engaging a pedicle screw driver, said pedicle screw being screwed into said medullary canal bore by screw driver.

17. A method according to claim 16, wherein said adaptor is fastened onto said proximal end of each said pedicle screw.

18. The method according to claim 17, wherein said adaptor is screwed in place onto said proximal end of each said pedicle screw.

19. The method according to claim 17, wherein said slotted cap of said adaptor is substantially flat and is fastened flush against the lumbar fascia of the patient.

20. The method according to claim 17, wherein a intervertebral disc between said vertebrae is removed and bone graphs are implanted before a plurality of beam members are inserted into each pair of associated adapters and locked into place.

21. The method according to claim 10, wherein said beam member is a plate or a rod.

22. The method according to claim 10, wherein said pedicle screws are implanted in the pedicles of adjacent thoracic vertebrae.

23. The method according to claim 10, wherein said pedicle screws are implanted in the pedicles of adjacent lumbar vertebrae.

24. The method according to claim 10, wherein said pedicle screws are implanted in the pedicles of adjacent thoracic and lumbar vertebrae.

25. The method according to claim 10, wherein said pedicle screws are implanted in the pedicles of the L5 and S1 vertebrae.

26. The method according to claim 10, wherein a plurality of beam members are positioned under the skin and onto the slotted caps and detachably locking said beam members into said caps.

27. A method for fixation of a pair of lumbar vertebrae of a patient, said patient having a back covered with skin under which is fascia, said patient also having lumbar vertebrae with cortical bone, transverse processes, proximal articular processes and pedicles, said pedicles having medullary canals, said method, comprising the steps of:

a) posterolaterally entering the back of a patient by means of forming a first mid-line incision with an open surgical technique and performing a laminectomy procedure at the site of the first incision;

b) forming a second paramedial incision through the fascia of a patient adjacent to the first incision;

c) forming an opening in the cortical bone of each said pair of lumbar vertebrae at a juncture of a base of the transverse process and the proximal articular process of said vertebrae, said openings in each pair of vertebrae providing entrances into the respective medullary canals of the pedicles supporting said vertebral processes;

d) screwing into each of said medullary canals a pedicle screw having a proximal end to a position where the proximal end thereof lies adjacent the fascia of the lumbar vertebrae of the patient, providing for each pedicle screw an adaptor having a slotted cap and a tubular body extending therefrom, said slotted cap lying in a plane perpendicular to said tubular body;

e) fastening the tubular body onto the proximal end of each said pedicle screws such that the slotted cap of the adaptor lies between the lumbar fascia and skin of the patient;

f) closing the second incision;

g) positioning at least one beam member under the skin and onto the slotted caps and detachably locking said beam member into said caps; and h) closing the first incision after the beam member is locked into the caps.

28. The method according to claim 27, wherein said vertebrae are aligned before insertion of said beam member, said beam member being locked in place to maintain said alignment.

29. The method according to claim 27, wherein one of the slotted caps has two ends which are open at both ends while the other slotted cap has two ends in which one end is open and the other end is closed, said beam member being slid through said open end of said one cap into said closed end of said other cap.

30. The method according to claim 27, wherein each said opening is formed by locating a selected opening position fluoroscopically, posterolaterally introducing a guide wire into a center of the pedicles and advancing said guide wire into said corical bone at said juncture; forming said opening and a bore in the said medullary canal with a pedicle tap means inserted over said guide wire and thereafter removing said guide wire and said tap means.

31. The method according to claim 30, wherein said pedicle screw is screwed into said medullary canal bore.

32. The method according to claim 31, wherein said proximal end of said pedicle screw includes means for engaging a pedicle screw driver, said pedicle screw being screwed into said medullary canal bore by screw driver.

33. A method according to claim 32, wherein said adaptor is fastened onto said proximal end of each said pedicle screw.

34. The method according to claim 33, wherein said adaptor is screwed in place onto said proximal end of each said pedicle screw.

35. The method according to claim 33, wherein said slotted cap of said adaptor is substantially flat and is fastened flush against the lumbar fascia of the patient.

36. The method according to claim 33, wherein a intervertebral disc between said vertebrae is removed and bone graphs are implanted before a plurality of beam members are inserted into each pair of associated adapters and locked into place.

37. The method according to claim 27, wherein said beam member is a plate or a rod.

38. The method according to claim 27, wherein said pedicle screws are implanted in the pedicles of adjacent thoracic vertebrae.

39. The method according to claim 27, wherein said pedicle screws are implanted in the pedicles of adjacent lumbar vertebrae.

40. The method according to claim 27, wherein said pedicle screws are implanted in the pedicles of adjacent thoracic and lumbar vertebrae.

41. The method according to claim 27, wherein said pedicle screws are implanted in the pedicles of the L5 and S1 vertebrae.

42. The method according to claim 27, wherein a plurality of beam members are positioned under the skin and onto the slotted caps and detachably locking said beam members into said caps.

* * * * *